United States Patent
Heise et al.

(10) Patent No.: US 11,439,956 B2
(45) Date of Patent: *Sep. 13, 2022

(54) METHOD FOR PROCESSING SOLUTIONS OF BIOMOLECULES

(71) Applicant: Fujifilm Diosynth Biotechnologies UK Limited, Billingham (GB)

(72) Inventors: Charles Heise, Billingham (GB); Tibor Nagy, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 34 days.

This patent is subject to a terminal disclaimer.

(21) Appl. No.: 16/864,234

(22) Filed: May 1, 2020

(65) Prior Publication Data
US 2020/0269190 A1    Aug. 27, 2020

Related U.S. Application Data

(63) Continuation of application No. 16/068,465, filed as application No. PCT/GB2016/053981 on Dec. 19, 2016, now Pat. No. 10,682,610.

(30) Foreign Application Priority Data

Jan. 7, 2016   (GB) ..................... 1600290

(51) Int. Cl.
*B01D 61/18* (2006.01)
*B01D 61/20* (2006.01)
(Continued)

(52) U.S. Cl.
CPC .......... *B01D 61/18* (2013.01); *B01D 61/142* (2013.01); *B01D 61/16* (2013.01); *B01D 61/20* (2013.01);
(Continued)

(58) Field of Classification Search
None
See application file for complete search history.

(56) References Cited

U.S. PATENT DOCUMENTS 3,726,613 A    4/1973   von Casimir
3,826,593 A    7/1974   Von Casimir
(Continued)

FOREIGN PATENT DOCUMENTS

WO    2015/133972 A1    9/2015
WO    2015/164511 A1    10/2015

OTHER PUBLICATIONS

Chargraff, et al., "The chemical constituents of blood platelets and their role in blood clotting, with remarks on the activation of clotting by lipids" in "Studies on teh Chemistry of Blood Coagulation." (1936) downloaded Apr. 23, 2020 from www.jbc.org (Year: 1936).
(Continued)

*Primary Examiner* — Chester T Barry
(74) *Attorney, Agent, or Firm* — Banner & Witcoff, Ltd.

(57) ABSTRACT

Apparatus for in-line liquid exchanging a biomolecule-containing liquid is provided. The apparatus comprises a means for mixing at least two liquids comprising a multiple inlet flow-controller, the means for mixing also comprising an outlet in fluid connection with a tangential flow filtration device configured in single-pass mode.

8 Claims, 2 Drawing Sheets

(51) Int. Cl.
*C07K 1/14* (2006.01)
*C12N 15/10* (2006.01)
*B01D 61/14* (2006.01)
*B01D 61/16* (2006.01)
*B01D 61/22* (2006.01)

(52) U.S. Cl.
CPC .......... *C07K 1/145* (2013.01); *C12N 15/1017* (2013.01); *B01D 61/22* (2013.01); *B01D 2313/18* (2013.01); *B01D 2313/19* (2013.01); *B01D 2313/243* (2013.01); *B01D 2315/10* (2013.01); *B01D 2315/16* (2013.01); *B01D 2317/022* (2013.01); *B01D 2319/022* (2013.01); *B01D 2321/2016* (2013.01); *B01D 2321/2066* (2013.01)

(56) References Cited

U.S. PATENT DOCUMENTS

| | | | |
|---|---|---|---|
| 4,492,531 A | 1/1985 | Kenji et al. | |
| 6,011,148 A | 1/2000 | Bussey et al. | |
| 6,062,829 A | 5/2000 | Ognier | |
| 7,682,511 B2 | 3/2010 | de los Reyes et al. | |
| 10,682,610 B2* | 6/2020 | Heise | B01D 61/142 |
| 2004/0256329 A1* | 12/2004 | Meserol | A61M 1/3683 |
| | | | 210/748.09 |
| 2007/0151924 A1* | 7/2007 | Mir | B01D 63/10 |
| | | | 210/637 |
| 2007/0151925 A1* | 7/2007 | de los Reyes | B01D 63/02 |
| | | | 210/641 |
| 2013/0040282 A1* | 2/2013 | Sehgal | A01N 1/0215 |
| | | | 435/2 |
| 2014/0263045 A1 | 9/2014 | Mazumdar et al. | |
| 2015/0183815 A1 | 7/2015 | Kopf et al. | |
| 2017/0173537 A1* | 6/2017 | Gagnon | C07K 1/34 |
| 2017/0298145 A1 | 10/2017 | Verkade et al. | |
| 2018/0296680 A1 | 10/2018 | Webber et al. | |
| 2018/0340010 A1 | 11/2018 | Hug et al. | |
| 2019/0046617 A1 | 2/2019 | Hanna et al. | |
| 2019/0277815 A1 | 9/2019 | Shinkazh | |

OTHER PUBLICATIONS

U.S. Appl. No. 61/983,186, filed by Oleg Shinkazh (Year: 2014).

* cited by examiner

METHOD FOR PROCESSING SOLUTIONS OF BIOMOLECULES

RELATED APPLICATIONS

This application is a Continuation Application of U.S. application Ser. No. 16/068,465, filed on Jul. 6, 2018, now U.S. Pat. No. 10,682,610, which is a National Stage Application under 35 U.S.C. 371 of co-pending PCT application PCT/GB2016/053981 designating the United States and filed Dec. 19, 2016; which claims the benefit of GB application number 1600290.9 and filed Jan. 7, 2016 each of which are hereby incorporated by reference in their entireties.

The present invention concerns a method for processing solutions of biomolecules, especially recombinant polypeptides and nucleic acids, and apparatus for carrying out such a method.

Many biomolecules, especially recombinant polypeptides and nucleic acids, such as plasmid (pDNA), have attracted much attention in particular for therapeutic applications. Such biomolecules are commonly produced by culturing recombinant host cells which have been engineered to express the desired biomolecule. The biomolecule is then recovered from the culture medium by methods typically comprising centrifugation, filtration, and chromatographic purification. The recovery of the biomolecule commonly comprises the adjustment of the nature and properties of the liquid medium in which the biomolecule is dissolved or suspended. This adjustment may facilitate purification of the biomolecule from impurities and/or the formulation of the biomolecule into a medium that can be, for example, stored pending either use or eventual conversion into a ready-for-use formulation. Such adjustment commonly comprises replacement of one liquid medium, commonly a buffer, with another, and may involve either a change in volume or not, in either case potentially also involving a change in concentration of the biomolecule.

Conventional liquid exchange involves the passing of an initial medium comprising the biomolecule through a tangential flow filtration device with an appropriately-sized molecular weight cut-off porous filter, the cut-off being selected such that the biomolecule is retained in the retentate, but that a portion of smaller components of the medium, for example buffer, solvent and solutes of molecular weight below the cut-off pass through the filter to the permeate. The retentate is recirculated to a holding tank where the retentate is mixed with a replacement, and the recirculation process continued until the medium comprising the biomolecule has the desired composition. The disadvantage of such a process is that as the scale of manufacture of the biomolecule increases, so the volumes of liquid that are required, and the scale of the storage and mixing tanks increase to the extent that the size and/or costs of the equipment are prohibitive. As an alternative, dialysis may be employed, where a porous bag having the required molecular-weight cut off is stored in a large volume of replacement liquid medium, but this suffers from similar disadvantages.

Further disadvantages of conventional processes are that the process is relatively slow, and hence slows down the processing of the biomolecule. In addition biomolecule instability and/or insolubility such as aggregation and denaturation can occur due to the biomolecules repeatedly passing through the pump head and experiencing shear forces across a broad range of solute and buffer concentrations as the process progresses.

Figure 1:
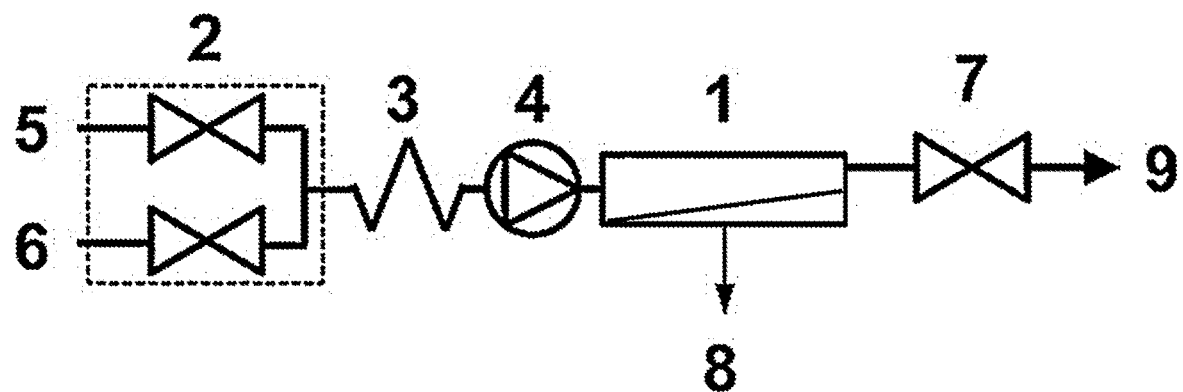
FIG. 1 shows one embodiment of the present invention comprising a single tangential flow device configured in single-pass mode.

According to a first aspect of the present invention, there is provided apparatus for in-line liquid exchanging a biomolecule-containing liquid comprising a means for mixing comprising a multiple inlet flow-controller further comprising two or more variable flow inlet valves for mixing at least two liquids, the flow-controller also comprising an outlet in fluid connection with a tangential flow filtration device (TFF device) configured in single-pass mode.

The means for mixing is preferably attached directly to the TFF device, ie no intermediate processing stage is incorporated in between.

In certain embodiments of the first aspect of the present invention, the retentate from the TFF device is in fluid connection with a second means for mixing at least two liquids. In other embodiments, one of multiple inlets in the multiple-inlet flow controller is in fluid connection with the retentate from a TFF device, the TFF device optionally being supplied by the outlet from a second means for mixing at least two liquids. In either embodiments, the second means for mixing may be of a different type to the first means for mixing, or may be the same type.

In further embodiments of the first aspect of the present invention, the second means for mixing comprises an outlet in fluid connection with a second TFF device. The second TFF device may be of a different type to the first TFF device, but in many embodiments, the first and second TFF devices are of the same type.

In yet further embodiments of the first aspect of the present invention, the retentate from the second TFF device is in fluid connection with a third means for mixing at least two liquids. The third means for mixing may be of a different type to the first and second means for mixing, or may be the same as either or both. The third means for mixing may comprises an outlet in fluid connection with a third TFF device. The third TFF device may be of a different type to the first and second TFF devices, but in many embodiments, the first, second and third TFF devices are of the same type.

It will be recognised that further means for mixing for at least two liquids, optionally with outlets in fluid connection with a TFF device may also be incorporated.

In many embodiments, each TFF device employed is configured in single pass mode, wherein none of the retentate is recirculated.

In certain embodiments, the apparatus includes a means for subjecting retentate to a recirculating tangential flow filtration step. Such a means may comprise a holding vessel and a separate TFF device configured to operate in recirculating mode. In some embodiments, two or more holding vessels with separate TFF devices configured to operate in recirculating mode are employed. In some embodiments, means are provided to enable one or more of the TFF devices employed in the apparatus according to the present invention to be operated in recirculating tangential flow filtration mode as an alternative to single pass mode. Such a recirculating tangential flow filtration step may be advantageous to define a discrete batch which can be advantageous when the product being produced is subject to stringent regulatory requirements, such as cGMP.

When two or more TFF devices are employed, each TFF device is preferably located in series.

The means for mixing comprising a multiple inlet flow-controller preferably comprises two or more variable flow, preferably intermittent flow, inlet valves which regulate the flow of liquid through the flow-controller.

Second and further means for mixing which can be employed include in-line mixers, including simple confluences between two tubes, wherein the tubes may have the same or differing diameters. The means for mixing may comprise baffles or vortex mixers. Each tube may be fitted with a means for imparting flow, such as a pump. The means for imparting flow may be operable in conjunction with the dimensions of the tubes, such that different flow rates of the at least two liquids can be achieved. In many embodiments, the second and subsequent means for mixing comprise multiple inlet flow-controllers, and preferably comprise two or more variable flow, preferably intermittent flow, inlet valves which regulate the flow of liquid through the flow-controller.

According to a second aspect of the present invention, there is provided apparatus for liquid exchanging a biomolecule-containing liquid comprising:
a) a multiple inlet flow-controller comprising:
 i) a first inlet for a first liquid medium comprising a biomolecule;
 ii) at least a second inlet for a second liquid medium;
 iii) an outlet in fluid connection with a tangential flow filtration device (TFF device); and
b) a means for imparting flow of the liquids through the flow-controller and the tangential flow filtration device.

Means for imparting flow of the liquids are well known in the art, and include the application of gas pressure to the liquid, especially an inert gas, such as nitrogen or helium. Preferably the means for imparting flow of the liquid is a pump. Pumps which can be employed include peristaltic, diaphragm, lobe and centrifugal pumps. Both disposable and re-usable pump designs can be employed. When a pump is employed, in many preferred embodiments, the pump is located between the outlet of the multiple inlet flow-controller and the TFF device. Two or more pumps may be employed, which may operate at the same or differing flow-rates. In certain embodiments the same flow rate achieved by each pump can be achieve through physically linking the pump heads and using the same tubing bore size or through synchronising the pumps to deliver the same flow rate through external control.

TFF devices that can be employed in the apparatus are well known in the art (see for example Filtration in the Biopharmaceutical Industry, ed. T. H. Meltzer and M. W. Jornitz, 1998) and include flat sheet, hollow fibre and annular wound devices. Preferably, the TFF device is a hollow-fibre filtration device.

The TFF device is selected to have a cut-off appropriate to the nature of the biomolecule, such that the biomolecule does not pass through a barrier, whereas smaller components of the liquid can pass through the barrier to the permeate.

The multiple inlet flow-controller comprises two or more variable flow, preferably intermittent flow, inlet valves which regulate the flow of liquid through the flow-controller. The multiple inlet flow-controller comprises at least 2 inlet valves and in many instances comprise up to 8, such as 3, 4, 5, 6 or 7, inlet valves. The inlet valves may each have the same dimensions, or one or more of the inlet valves may have different dimensions. In certain preferred embodiments, the volume measured from each inlet valve to the outlet of the flow-controller is the same for each inlet, and it is highly preferred that both the volume and the path length measured from each inlet valve to the outlet of the flow-controller is the same for each inlet.

The flow-controller employed in the present invention also comprises at least one outlet, and whilst two or more outlets may be present, it is preferred that a single outlet is employed.

The variable flow valves may regulate the flow between a first, relatively low flow rate wherein the liquid remains able to flow and at least a second, higher flow rate. In preferred embodiments, the variable flow valve is an intermittent flow valve, which prevents flow in a first position, but permits flow in at least a second position. Most preferably, all of the valves are intermittent flow valves.

Preferably the variable flow valves are controlled, most preferably by a programmable control unit, to regulate the opening and closing of the valves in order to achieve the required relative quantities of the input liquids flowing through the multiple inlet flow-controller. This is preferably achieved through cycling, with a pre-determined time period or cycle rate, through the inlet valves in the flow-controller and regulating the opening or closing of the valve according to the required proportion of the cycle time to generate the desired composition. The cycle rate can be either constant or varied. Most preferably, intermittent flow inlet valves are employed, and are controlled such that in operation, only one valve is open at any given time. In many embodiments, the cycle rate of the multiple inlet flow-controller is maintained as a constant and the desired relative quantities of the input liquids remains consistent.

In many embodiments, multiple cycles are employed. The number of cycles employed will depend on numerous factors such as the duration of the process, the volume of liquid being concentrated, the flow rate, the maximum operating pressure of the apparatus, the length and/or area of the TFF device and the molecular weight cut-off for the TFF device. In certain embodiments, at least 10 cycles, such as at least 50, 100, 500, 750, 1000, 1500, 2000, 3000, 5000, 7500, 10000 or more cycles can be employed.

It will be recognised that a range of cycle frequencies can be employed. In many instances, the frequency is less than 100 Hz, typically less than 50 Hz, commonly less than 10 Hz, and preferably less than 5 Hz. In certain preferred embodiments, the frequency is 2 Hz or less, most preferably 1 Hz or less, such as from 0.05 to 0.5 Hz.

During the operation of a TFF device, it is common for a gel layer comprising biomolecule to form on the retentate side of the filter surface. This gel layer is typically removed from the TFF device by the inclusion of a flush at the end of the operation, and such a flush step can be employed in the process of the present invention. A flush step at the end of the operation can result in significant spike in the concentration of biomolecule, and therefore may result in a higher than expected biomolecule concentration. In certain embodiments of the present invention, flush stages are included at intervals throughout the process. A flush stage may comprise extending the period at which the liquid passes through the TFF device at the lower pressure, and may additionally comprise prevention of permeate flow, such that all flow passes to the retentate such as by closing a valve on the permeate line, preferably for the duration of the flush. The duration of a flush stage is often selected to achieve transfer of substantially all of the gel layer into the retentate. A flush stage at the end of the operation may comprise passing up to five TFF device volumes. Flush stages included at intervals in the process may comprise passing lower TFF device volumes, such as 0.25, 0.5. 0.75 or 1 TFF device volumes. In some embodiments, a flush stage is employed after operation of cycling for the passage of 1 TFF device volume, 2 TFF device volumes, 5 TFF device volumes, 10 TFF device volumes or more, followed by a return to operation of cycling. In many embodiments where one or more flush stages are incorporated at intervals in the concentration process, the flush stage is accompanied by prevention of permeate flow, such as by closing a valve on the permeate line, preferably for the duration of the flush.

The apparatus commonly comprises a restrictor, such as a flow-restricting orifice or pinch valve downstream of the TFF device. The restrictor is configured to provide a flow restriction and therefore back-pressure such that liquid and solutes with molecular weights less than the molecular weight cut-off of the TFF device passes through the membrane to the permeate. Preferably, the restrictor comprises a pinch valve, which according to one aspect of the present invention can be controllable. In certain embodiments, the restrictor comprises a second multiple inlet flow-controller, preferably comprising variable flow valves. In some embodiments, the restrictor comprises a pump downstream of the TFF device which is configured to operate at a lower flow rate than the flow rate into the TFF device, thereby generating back-pressure.

When the restrictor comprises a second multiple inlet flow controller comprising variable flow valves, cycling is preferably employed. Cycle times and frequencies employed can be as described above for the first multiple inlet flow controller comprising variable flow valves.

The apparatus according to the second aspect of the present invention optionally comprises an in-line mixer, which may be located between the valve and the concentrator, and is preferably located between the valve and pump. Examples of in-line mixers are well known in the art. Preferred in-line mixers are static mixers such as baffled mixers and vortex mixers. The dimension of the mixer are preferably selected such that the input liquids are adequately mixed prior to entry into the TFF device.

It will be recognised that the combining of the liquids through the flow-controller dilutes the concentration of the biomolecule in the first liquid. The extent of this dilution is controlled by the relative volumes of the liquids passing through the inlets, and this in turn is controlled by the relative dimensions of the inlets and/or the relative times the inlets are retained at their higher flow rate and their lower flow rate. The dilution of the biomolecule effected by the mixing of the liquids can be at least partially off-set, and may be completely off-set, or even more than off-set by the passage of the combined liquids through the TFF device. The apparatus may be configured such that the relative portion of the combined liquids passing through the TFF device as retentate is greater than, equal to, or less than the portion passing through into the permeate. When the ratio of the volume of liquid passing into the permeate to the volume passing as retentate is equal to the ratio of the volume of second and additional liquids combined to the volume of the first liquid comprising the biomolecule, the concentration of biomolecule in the retentate will be the same as the initial concentration in the first liquid. Increasing the volume ratio of permeate to retentate to be higher than the volume ratio of second and additional liquids to the first liquid will increase the concentration of biomolecule in the retentate relative to the concentration in the first liquid, whereas reducing the volume ratio of permeate to retentate to be lower than the volume ratio of second and additional liquids to the first liquid will decrease the concentration of biomolecule relative to the concentration in the first liquid. For example, where the first liquid comprising a biomolecule is diluted 10-fold with a second liquid by use of a 1:9 ratio of first to second liquid, and then the volume ratio of permeate to retentate is 9:1, the biomolecule is back at its original concentration, with a 90% clearance $[(10-1)/10\times100]$ of the first liquid being achieved. Repeating this process in a second step exchange would give a 99% clearance of the first liquid $[9((10\times10)-1)]/(10\times10)\times100]$ but retain the original biomolecule concentration. However, if the volume ratio of permeate to retentate is 19:1 on the concentrators and dilution remained at 1:9, the concentration of biomolecule would be increased two-fold through a first step with the same 90% clearance of the first liquid, and four-fold through a second step with the same 99% clearance of the first liquid, whilst if the volume ratio of permeate to retentate is 4:1 on the concentrators and dilution remained at 1:9, the concentration of biomolecule would be decreased two-fold through a first step with the same 90% clearance of the first liquid, and four-fold through a second step with the same 99% clearance of the first liquid.

In many embodiments, the volume ratio of first liquid to second and subsequent liquids flowing through the flow-controller is controlled by controlling the opening times of controllable intermittent flow valves regulating the flow of the relevant liquids. Preferably a pump located downstream of the flow-controller controls the flow rate through the flow-controller, and where the flow paths of the valves to the outlet are of equal volume, the relative volumes are governed by the opening times of the valves. All other things being equal, the smaller the time that the first liquid valve is open relative to the other valves, the higher the exchange for the second and additional liquids.

In certain embodiments, a second TFF device, preferably configured according to the present invention, is located downstream of the first TFF device. In many such instances, the multiple inlet flow-controller for the second TFF device serves as a restrictor for the first TFF device. Further TFF devices, preferably configured according to the present invention, may be located downstream of the second TFF device. When second or further TFF devices configured according to the present invention are employed, an inlet for the multiple inlet flow-controller is in fluid connection, preferably direct connection, with the retentate from the TFF device upstream. For the second or further TFF devices configured according to the present invention, the inlet for the corresponding second liquid medium may comprise an inlet for the same liquid medium as for the first TFF device, or may comprise an inlet for a different liquid medium.

The apparatus according to the present invention can be employed for conditioning of solutions or suspensions of biomolecules, for example feed streams, such as changing the conductivity and/or pH, buffer exchange, changing constituent solutes, and changing volumes to alter, and preferably reduce, processing time of the downstream unit operation, for example chromatography load times. In certain instances, the apparatus according to the present invention may be used for refolding of polypeptides, or for pDNA extraction.

Using the apparatus according to the present invention, liquid exchange can be achieved without recirculation of the retentate.

Liquids employed in the present invention may be eluent from purification methods (for example, chromatography columns, conventional TFF steps, filtration and clarification steps, centrifuge supernatant/centrate or slurries, conditioning/dilution steps, output from bioreactors and fermenters, and output from cell disruption processes.

Liquids produced by the apparatus and processes of the present invention can be used "as is" with no further processing, or may be subject to one of more further processing steps, such as purification or processing steps, for example chromatography steps, such as affinity chromatography, anion and/or cation exchange chromatography, hydrophobic interaction chromatography, size-exclusion chromatography, affinity chromatography; and/or further filtration, clarification, conditioning, dilution or other formulation steps.

The apparatus according to the present invention can be employed for concentration of liquids comprising biomolecules, for example pDNA, inclusion bodies, particularly inclusion bodies comprising polypeptides, and especially recombinant polypeptides.

pDNA may be in one or more of multiple forms, such as supercoiled, linear and open-circular (i.e. nicked or relaxed) isoforms. Supercoiled pDNA isoform has a covalently closed circular form and the pDNA is negatively supercoiled in the host cell by the action of host enzyme systems. In the open-circular isoform, one strand of the pDNA duplex is broken at one or more places.

Methods for the production of pDNA are well known in the art. pDNA may be natural or artificial, for example, cloning vectors carrying foreign DNA inserts. In many embodiments, the pDNA is in the size range of 1 kilobase to 50 kilobases. For example pDNA encoding expressed interfering RNA is typically in the size range of 3 kilobases to 4 kilobases.

Polypeptides, especially recombinant polypeptides, include therapeutic proteins and peptides, including cytokines, growth factors, antibodies, antibody fragments, immunoglobulin like polypeptides, enzyme, vaccines, peptide hormones, chemokines, receptors, receptor fragments, kinases, phosphatases, isomerases, hydrolyases, transcription factors and fusion polypeptides.

Antibodies include monoclonal antibodies, polyclonal antibodies and antibody fragments having biological activity, including multivalent and/or multi-specific forms of any of the foregoing.

Naturally occurring antibodies typically comprise four polypeptide chains, two identical heavy (H) chains and two identical light (L) chains inter-connected by disulfide bonds. Each heavy chain comprises a variable region ($V_H$) and a constant region ($C_H$), the $C_H$ region comprising in its native form three domains, $C_H1$, $C_H2$ and $C_H3$. Each light chain comprises a variable region ($V_L$) and a constant region comprising one domain, CL.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Antibody fragments which can be expressed comprise a portion of an intact antibody, said portion having a desired biological activity. Antibody fragments generally include at least one antigen binding site. Examples of antibody fragments include: (i) Fab fragments having $V_L$, $C_L$, $V_H$ and $C_H1$ domains; (ii) Fab derivatives, such as a Fab' fragment having one or more cysteine residues at the C-terminus of the $C_H1$ domain, that can form bivalent fragments by disulfide bridging between two Fab derivatives; (iii) Fd fragment having $V_H$ and $C_H1$ domains; (iv) Fd derivatives, such as Fd derivatives having one or more cysteine residues at the C-terminus of the $C_H1$ domain; (v) Fv fragments having the $V_L$ and $V_H$ domains of a single arm of an antibody; (vi) single chain antibody molecules such as single chain Fv (scFv) antibodies in which the $V_L$ and $V_H$ domains are covalently linked; (vii) $V_H$ or $V_L$ domain polypeptide without constant region domains linked to another variable domain (a $V_H$ or $V_L$ domain polypeptide) that is with or without constant region domains, (e.g., $V_H$—$V_H$, $V_H$—$V_L$, or $V_L$—$V_L$) (viii) domain antibody fragments, such as fragments consisting of a $V_H$ domain, or a $V_L$ domain, and antigen-binding fragments of either $V_H$ or $V_L$ domains, such as isolated CDR regions; (ix) so-called "diabodies" comprising two antigen binding sites, for example a heavy chain variable domain ($V_H$) connected to a light chain variable domain ($V_L$), in the same polypeptide chain; and (x) so-called linear antibodies comprising a pair of tandem Fd segments which, together with complementary light chain polypeptides, form a pair of antigen binding regions.

Inclusion bodies include insoluble aggregates formed in the cytoplasm of bacterial cells such as *E. coli*, most commonly comprising polypeptide and especially recombinant polypeptide.

In addition to a target biomolecule, other components of the biomolecule-containing liquid may include salts, including buffer salts, culture media and feed components, solvents, commonly water, co-solvents, such as $C_{1-6}$ polyols, such as propylene glycols and sorbitol, ionic liquids, zwittergens, surfactants, imidazole or other competitive ligand binders, amino acids, chaotropic agents, such as urea, reductants, oxidants, PEGylation conjugation reactants (substrates, by-products and activators), sugars, lipids, nucleic acids, metabolites and small polypeptides. Liquids mixed with the first biomolecule-containing liquid are free from the target biomolecule, and in many embodiments are free from proteins and nucleic acids. Components of liquids mixed with the biomolecule-containing liquid commonly include salts, including buffer salts, culture media and feed components, solvents, commonly water, co-solvents, such as $C_{1-6}$ polyols, such as propylene glycols and sorbitol, ionic liquids, zwittergens, surfactants, imidazole or other competitive ligand binders, amino acids, chaotropic agents, such as urea, reductants, oxidants and sugars.

One example of apparatus according to the present invention is illustrated in FIG. 1. A TFF device, 1, is located downstream of a multiple inlet variable flow-controller, 2, static mixer, 3, and a pump, 4, which supplies a liquid feed to the TFF device, 1. The multiple inlet variable flow-controller, 2, controls the feed of a first liquid comprising a biomolecule, 5, and a second liquid, 6, into the TFF device, 1. A restrictor, 7, is located on the retentate line from the TFF device, 1. Cycling of each intermittent flow valve in the multiple inlet variable flow-controller, 2, between closed and open positions causes dilution of the biomolecule. On passing through the TFF device, 1, pressure caused by the action of the pump, 4, and the restrictor, 7, causes a portion of the liquid below the molecular weight cut-off of the TFF device, 1, to pass into the permeate, 8, resulting in an increase in the concentration of the biomolecule in the retentate, 9.

Figure 2:
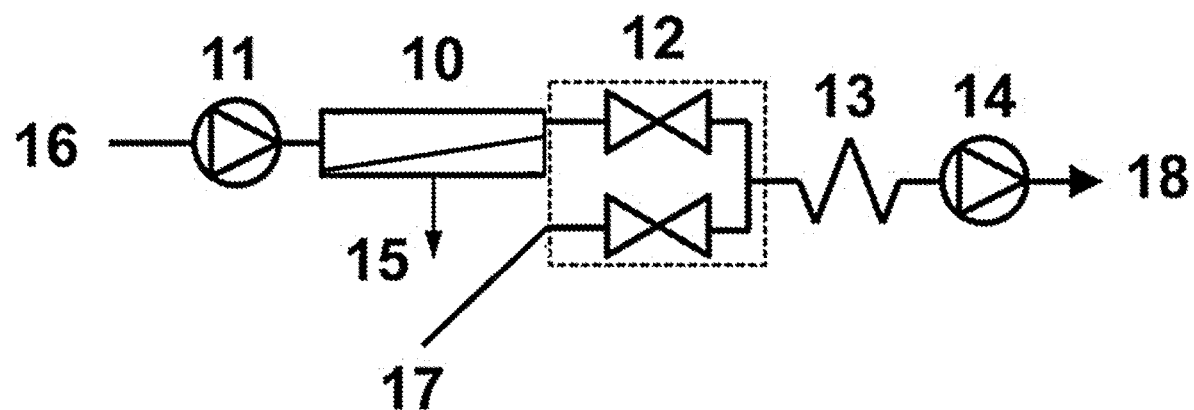
FIG. 2 shows another embodiment of the present invention comprising a single tangential flow device configured in single-pass mode.

Another example of apparatus according to the present invention is illustrated in FIG. 2. A TFF device, 10, is located downstream of a pump, 11, which supplies a liquid feed to the TFF device, 10, and upstream of a multiple inlet variable flow-controller, 12, static mixer, 13, and a second pump, 14. On passing through the TFF device, 10, pressure caused by the action of the pump, 11, and the multiple inlet variable flow-controller, 12, causes a portion of the liquid below the molecular weight cut-off of the TFF device, 10, to pass into the permeate, 15, resulting in an increase in the concentration of the biomolecule entering the multiple inlet variable flow-controller, 12. The intermittent flow valves in the multiple inlet variable flow-controller, 12, controls the feed of a first liquid comprising a biomolecule, 16, and a second liquid, 17. Cycling of each intermittent flow valve in the multiple inlet variable flow-controller, 12, between closed and open positions causes dilution of the concentrated biomolecule through the action of the second pump, 14, located on the retentate line, 18, from the TFF device, 10. The static mixer, 13, upstream of the second pump, 14, ensures the retentate, 18, is homogeneous in composition for the second liquid and biomolecule.

Figure 3:
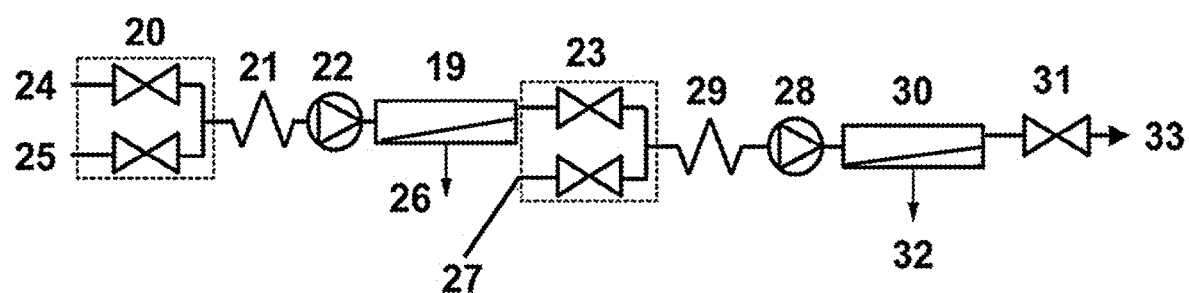
FIG. 3 shows one embodiment of the present invention comprising two tangential flow devices configured in single-pass mode.

A further example of the present invention using two TTF devises is illustrated in FIG. 3. The first TFF device, 19, is located downstream of the first multiple inlet variable flow-controller, 20, static mixer, 21, and pump, 22, which supplies a liquid feed to the first TFF device, 19. A second multiple inlet variable flow-controller, 23, is located downstream on the retentate line from the first TFF device, 19. The first multiple inlet variable flow-controller, 20, controls the feed of a first liquid comprising a biomolecule, 24, and a second liquid, 25, into the TFF device, 19. Cycling of each intermittent flow valve in the multiple inlet variable flow-controller, 20, between closed and open positions causes dilution of the biomolecule. On passing through the first TFF device, 19, pressure caused by the action of the pump, 22, and the second multiple inlet variable flow-controller, 23, causes a portion of the liquid below the molecular weight cut-off of the first TFF device, 19, to pass into the permeate, 26, resulting in an increase in the concentration of the biomolecule entering the second multiple inlet variable flow-controller, 23. The second intermittent flow valves in the multiple inlet variable flow-controller, 23, controls the feed of the concentrated biomolecule from the first TFF device, 19, and a third liquid, 27. Cycling of each intermittent flow valve in the second multiple inlet variable flow-controller, 23, between closed and open positions causes dilution of the concentrated biomolecule through the action of the second pump, 28, located downstream of both a second static mixer, 29, and the second multiple inlet variable flow-controller, 23, outlet. The second pump, 28, supplies a liquid feed to the downstream second TFF device, 30. A restrictor, 31, is located on the retentate line from this second TFF device, 30. On passing through the second TFF device, 30, pressure caused by the action of the second pump, 28, and the restrictor, 31, causes a portion of the liquid below the molecular weight cut-off of the TFF device, 30, to pass into the permeate, 32, resulting in an increase in the concentration of the biomolecule in the retentate, 33.

Figure 4:
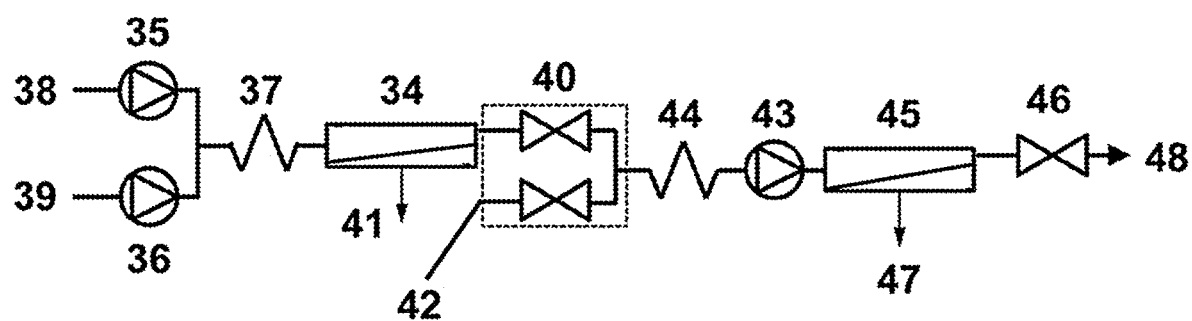
FIG. 4 shows another embodiment of the present invention comprising two tangential flow devices configured in single-pass mode.

Another further example of the present invention using two TTF devices is illustrated in FIG. 4. The first TFF device, 34, is located downstream of two feed pumps, 35 and 36, and a static mixer, 37, which supplies the liquid feed to the first TFF device, 34. The first pump, 35, controls the feed of a first liquid comprising a biomolecule, 38, and the second pump, 36, controls the feed of a second liquid, 39, into the first TFF device, 34. The action of the two pumps, 35 and 36, causes dilution of the biomolecule. A multiple inlet variable flow-controller, 40, is located downstream on the retentate line from the first TFF device, 34. On passing through the first TFF device, 34, pressure caused by the action of the pumps, 35 and 36, and the multiple inlet variable flow-controller, 40, causes a portion of the liquid below the molecular weight cut-off of the first TFF device, 34, to pass into the permeate, 41, resulting in an increase in the concentration of the biomolecule entering the multiple inlet variable flow-controller, 40. The intermittent flow valves in the multiple inlet variable flow-controller, 40, controls the feed of the concentrated biomolecule from the first TFF device, 34, and a third liquid, 42. Cycling of each intermittent flow valve in the second multiple inlet variable flow-controller, 40, between closed and open positions causes dilution of the concentrated biomolecule through the action of the third pump, 43, located downstream of both a second static mixer, 44, and the multiple inlet variable flow-controller, 40, outlet. The third pump, 43, supplies a liquid feed to the downstream second TFF device, 45. A restrictor, 46, is located on the retentate line from this second TFF device, 45. On passing through the second TFF device, 45, pressure caused by the action of the second pump, 43, and the restrictor, 46, causes a portion of the liquid below the molecular weight cut-off of the TFF device, 45, to pass into the permeate, 47, resulting in an increase in the concentration of the biomolecule in the retentate, 48.

The present application is illustrated without limitation by the following examples.

Abbreviations

DV Diavolumes
mPES modified Polyethylenesulfone
rhLactoferrin recombinant human Lactoferrin
TFF Tangential Flow Filtration
Protein Model:
  Purified rhLactoferrin at an initial concentration of 1 mg/mL in 50 mM sodium phosphate pH 7.5 was used in the experimental studies.
  Buffer (A) 50 mM sodium phosphate, 0.1 M NaCl, pH 7.0
  Buffer (B) 50 mM sodium phosphate, pH 7.5
  Buffer (C) 50 mM sodium phosphate, 0.1M NaCl, 10% sorbitol, pH 7.0
  Buffer (D) 50 mM sodium phosphate, 0.1M NaCl, 10% sorbitol, 6% propane-1,2-diol, pH 7.0

Example 1

A stock of at least 400 mL of 1 mg/mL rhLactoferrin at pH 7.5 was volumetrically diluted 4-fold with buffer (A) through using a 25% gradient of rhLactoferrin on the B1 pump of a GE Healthcare ÄKTA™ Explorer system, whilst feeding buffer (A) through the A1 pump (75%) at a constant flow rate of 15 mL/min. The diluted rhLactoferrin was then directed in down flow mode through position 2 on the ÄKTA™ Explorer V2 valve into a 65 cm long, 10 kDa mPES Spectrum Labs MidiKros™ hollow fibre with a surface area of 370 cm². The hollow fibre retentate line was in turn directly connect to a downstream multiple inlet variable flow-controller. The multiple inlet variable flow-controller comprises of a custom made (Gemü) plastic two valve manifold with a single outlet having a 2 mm internal bore with a fast acting solenoid actuator under the control of a Raspberry Pi minicomputer, which controls the flow of liquid through the manifold. The manifold is configured to have the same flow path volumes from valve to the outlet. The cycle time of the multiple inlet variable flow-controller was set to 2 seconds and the retentate controlling valve was opened for 25% of the cycle to achieve the 4-fold volumetric concentration factor required to obtain the initial starting volume of the rhLactoferrin solution. The second valve position on the multiple inlet flow-controller was open for the 75% of the cycle when the first valve was closed, to allow a second 4-fold dilution of the hollow fibre retentate with buffer (B). The outlet from the multiple inlet variable flow-controller passed through a static mixer of length 10 cm and diameter 5 mm before return to valve V3, position 2 on the ÄKTA™ Explorer to collect conductivity, pH and 280 nm absorbance data. The F8 outlet line from the ÄKTA™ Explorer valve V4 was connected to the A11 feed line of the A1 pump of a second GE Healthcare ÄKTA™ Explorer system also running at 15 mL/min. This system was in turn connected to a second 65 cm long, 10 kDa mPES Spectrum Labs MidiKros™ hollow fibre with a surface area of 370 cm$^2$ through the ÄKTA™ Explorer column valve V2, again on position 2. The retentate of the hollow fibre was fed directly into a second 10 mm internal bore sized multiple inlet variable flow-controller. This valve used a cycle time of 10 seconds with retentate controlling valve being open for 4% of the cycle to obtain the 4-fold volumetric concentration factor in order to once again obtain the initial starting volume of the rhLactoferrin solution. The outlet from the multiple inlet variable flow-controller was directed through a second static mixer of length 10 cm and diameter 5 mm before returning to the ÄKTA™ explorer on valve V3, position 2 for collection of conductivity, pH and 280 nm absorbance data. The in-line buffer exchanged rhLactoferrin solution was collected through the outlet line F8 on the ÄKTA™ Explorer valve V4. The data from the first ÄKTA™ Explorer system demonstrated successful rapid buffer exchange using an in-line system, whilst the trace from the second ÄKTA™ Explorer system showed the protein concentration relative to the feed was maintained.

Absorbance, conductivity and pH traces of the in-line buffer exchanged rhLactoferrin demonstrates using two 4-fold dilutions and concentrations resulted in a ~95% exchange of buffer (A) for buffer (B). Buffer (B) conductivity 6.9 mS/cm and pH 7.47 compared well with final buffer exchanged Lactoferrin with a conductivity 7.2 mS/cm and pH 7.43. The protein concentration was maintained at around 45 mAU.

Examples 2 to 8

The method of Example 1 was repeated, but with the conditions varied as stated in Table 1 to investigate the effect of reversing the buffer exchange or the addition of buffer components which change buffer viscosity (10% sorbitol and/or 6% propan-1,2-diol) on the operating time and different concentration/dilution ratios between the $1^{st}$ and $2^{nd}$ concentrators. Examples 2 and 3 used buffer (A) for the diluent, Example 4 used buffer (B), Examples 5, 6 and 7 used buffer (C) and Example 8 used buffer (D).

From the results given in Table 1, it can be seen that serial dilution and concentration achieves buffer exchanges equivalent to up to 3 diavolumes on a conventional re-circulating batch TFF system. Higher buffer exchange efficiencies can be achieved by running at greater dilution rates, as seen in Examples 6 and 7.

TABLE 1

| Ex. | Combined dilution ratio | Conductivity | | | | | Feed (mL) | Retentate (mL) |
|---|---|---|---|---|---|---|---|---|
| | | Feed (mS/cm) | Buffer (mS/cm) | Retentate (mS/cm) | Efficiency (%) | Equivalent DV | | |
| 1 | 1:16 | 3.57 | 16.49 | 16.14 | 97.9 | 3.9 | 65.7 | 243 |
| 2 | 1:16 | 3.64 | 16.49 | 14.48 | 87.8 | 2.1 | 67.5 | 48 |
| 3 | 1:16 | 3.64 | 16.49 | 14.76 | 89.5 | 2.3 | 345 | 550 |
| 4 | 1:16 | 14.20 | 7.02 | 7.96 | 86.6 | 2.0 | 350 | 770 |
| 5 | 1:16 | 9.34 | 15.15 | 14.70 | 97.0 | 3.5 | 159 | 220 |
| 6 | 1:16 | 9.42 | 15.54 | 14.63 | 94.1 | 2.8 | 154 | 224 |
| | 1:32 | | | 14.90 | 95.9 | 3.2 | | |
| 7 | 1:12 | 9.42 | 15.54 | 14.36 | 92.4 | 2.6 | 242 | 251 |
| | 1:16 | | | 14.64 | 94.2 | 2.8 | | |
| | 1:24 | | | 14.88 | 95.8 | 3.2 | | |
| | 1:32 | | | 14.99 | 96.5 | 3.4 | | |
| 8 | 1:16 | 14.82 | 11.44 | 12.56 | — | — | 126 | 157 |

The invention claimed is:

1. Apparatus for in-line liquid exchanging a biomolecule-containing liquid comprising a means for mixing comprising a multiple inlet flow-controller further comprising two or more variable flow inlet valves for mixing at least two liquids, wherein the variable flow inlet valves are controlled to be cycled between a position achieving a first, relatively low flow rate wherein the liquid remains able to flow, or flow is prevented and at least a second, higher flow rate, the means for mixing also comprising an outlet in fluid connection with a tangential flow filtration device configured in single-pass mode.

2. The apparatus according to claim 1, wherein the variable flow inlet valves are intermittent flow valves.

3. Apparatus for liquid exchanging a biomolecule-containing liquid comprising:
  a) a multiple inlet flow-controller comprising:
    i) a first inlet for a first liquid medium comprising a biomolecule;
    ii) at least a second inlet for a second liquid medium;
    iii) an outlet in fluid connection with a tangential flow filtration device; and
  b) a means for imparting flow of the liquids through the flow-controller and the tangential flow filtration device, and
  c) a means for controlling the flow through the tangential flow filtration device such that the flow is cycled between a position achieving a first, relatively low flow rate wherein the liquid remains able to flow, or flow is prevented and at least a second, higher flow rate.

4. The apparatus according to claim 3, further comprising a second multiple inlet flow-controller comprising:
   i) a first inlet in fluid connection with the retentate from the tangential flow filtration device;
   ii) a second inlet for a third liquid medium; and
   iii) an outlet in fluid connection with a second tangential flow filtration device.

5. The apparatus according to claim 4, wherein the second multiple inlet flow-controller functions as a restrictor.

6. The apparatus according to claim 5, wherein the second multiple inlet flow-controller further comprises two or more variable flow inlet valves.

7. A method for the preparation of a biomolecule, which comprises processing a liquid medium comprising the biomolecule by liquid exchange employing an apparatus according to claim 1, wherein at least 10 cycles are employed, the cycle frequency is less than 100 Hz, and the processing comprises buffer exchange.

8. The method according to claim 7, wherein the cycle frequency is from 0.05 to 0.5 Hz.

* * * * *